United States Patent [19]

Ross et al.

[11] 4,161,337

[45] Jul. 17, 1979

[54] PORTABLE FOLDING ORTHOPEDIC CHAIR

[75] Inventors: Albert Ross, Palm Springs; Richard H. Garrett, Berkeley; Hayden S. Gordon, Orinda; Evan R. Flavell, Albany, all of Calif.

[73] Assignee: Albert Ross, Palm Springs, Calif.

[21] Appl. No.: 860,985

[22] Filed: Dec. 15, 1977

[51] Int. Cl.² ............................................. A47C 7/40
[52] U.S. Cl. ................................... 297/230; 297/284; 297/460
[58] Field of Search ............... 297/230, 231, 284, 381, 297/382, 183, 353, 460

[56] References Cited

U.S. PATENT DOCUMENTS

| | | | |
|---|---|---|---|
| 567,096 | 9/1896 | Harvey et al. | 297/231 |
| 1,011,026 | 12/1911 | Carpenter | 297/460 |
| 1,228,771 | 6/1917 | Hanger | 297/284 |
| 2,304,349 | 12/1942 | Fox | 297/231 |
| 2,858,876 | 11/1958 | Woodson | 297/353 |
| 2,942,651 | 6/1960 | Binding | 297/284 |
| 3,014,761 | 12/1961 | Otto | 297/230 |
| 3,295,888 | 1/1967 | Poland | 297/353 |
| 3,326,602 | 6/1967 | Moore et al. | 297/353 |
| 4,036,525 | 7/1977 | Howk | 297/353 |
| 4,047,757 | 9/1977 | Eames et al. | 297/230 |

*Primary Examiner*—Francis K. Zugel
*Attorney, Agent, or Firm*—Owen, Wickersham & Erickson

[57] ABSTRACT

A portable folding orthopedic seat unit for use on a chair, automobile seat, or the like. A semirigid seat member is hinged to a back member. Vertical rigid support means extends from the bottom to the top of the back member and supports a back-support assembly, comprising two separate, generally elliptically-shaped, padded back-support members, spaced apart from each other, and a substantially vertically rigid and laterally flexing connecting member joining them together. The connecting member serves to transfer forces from one back-support member to the other. Releasable locking means holds the assembly at a selected vertical position on the rigid support means.

5 Claims, 7 Drawing Figures

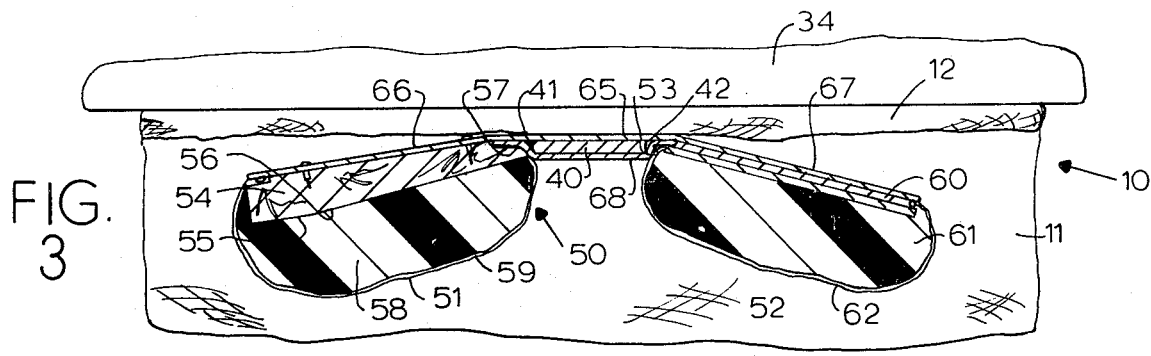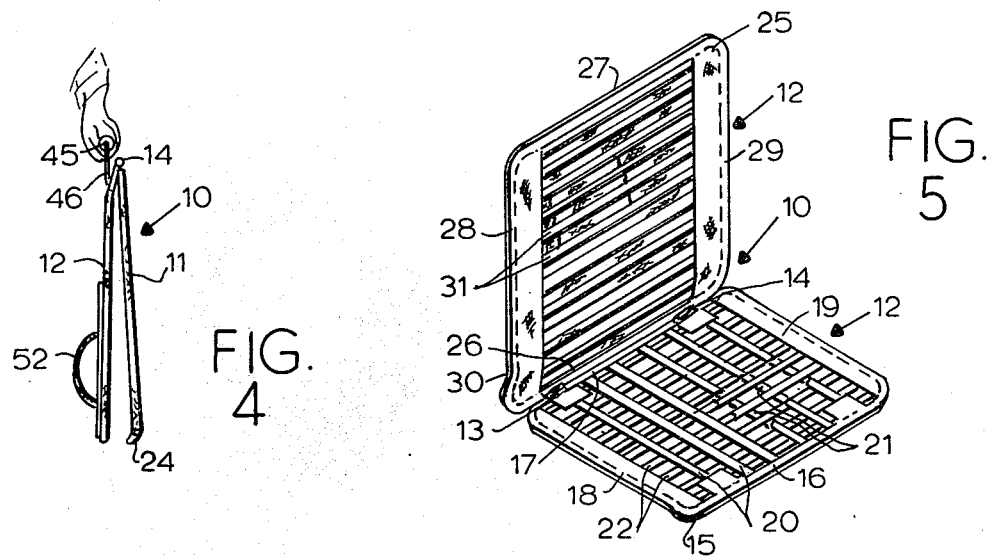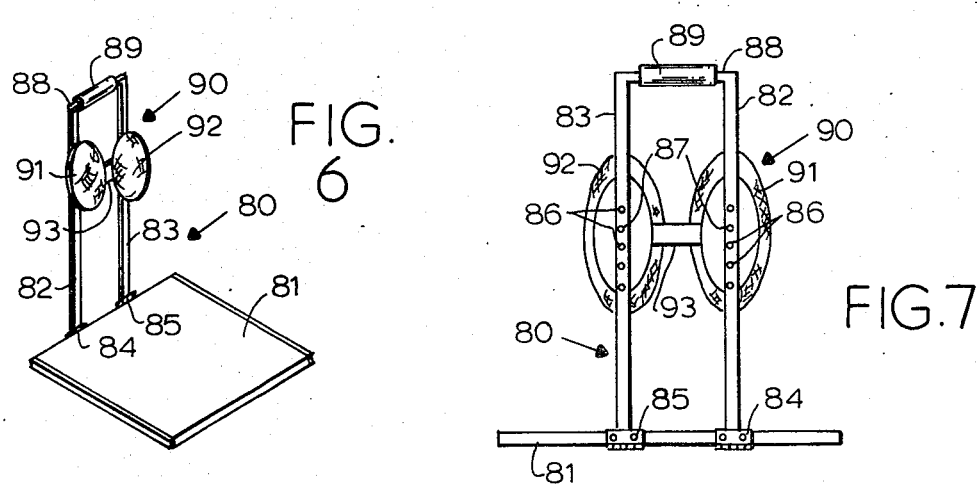

PORTABLE FOLDING ORTHOPEDIC CHAIR

BACKGROUND OF THE INVENTION

This invention relates to an improved portable orthopedic seat unit insert for providing support for the lower back of the sitter and for relieving lower-back discomfort.

Seat inserts heretofore in use have generally been for the purpose of obtaining ventilation to the rear of or under the sitter or to provide cushioning. They have generally provided merely a flat back portion and a flat seat portion hinged together. They have usually not sought any special approach to support of the lower back and therefore have not usually had any special shaping. Even when they have attempted to provide some lower-back support they have provided for little, if any, possibility of adjustment to adapt the unit for different individuals.

For example, the Manley U.S. Pat. No. 2,081,111 shows an automobile cushion wherein two back-support pads are immovably mounted to a canvas backing. Such adjustment as there is, is obtained by moving the canvas backing up and down the seat. If the user moves his position, he risks shifting the position of the cushion or letting it slide down toward the seat.

The Sopko, Jr., U.S. Pat. No. 3,145,054 shows a folding portable chair seat with a back-supporting pneumatic cushion that extends laterally across the back and engages the spine along the small of the back. It is not adjustable as to height but only as to the amount of inflation.

These devices do not solve the problem to which the present invention is directed because they lack the necessary adjustment for enabling adaption to different people or even for different times for the same person. Moreover, they do not apply the support to the exact locations where support is needed.

A great many people find regular chairs and sofas uncomfortable and ordinary automobile seats unbearable. For example, for a long cross-country flight in a commercial airline, although many people may find the seats sufficiently comfortable, there are also many who find them unduly uncomfortable and view the taking of such a trip as a very uncomfortable experience. Similarly, many people find that their automobile seats lack comfort; most people put up with the discomfort, but those who have a back problem find riding in such seats very difficult, and they often find prolonged driving to be an excruciating experience.

An important object of the present invention is to provide a portable orthopedic seat insert which greatly adds to the comfort of the sitter, especially one having back problems.

Another object of the invention is to devise a seat insert which provides adequate support where it is needed, —on each side of the lower part of the back- —and thereby relieves lower-back discomfort.

Another object is to provide a readily portable folding seat insert which can be taken aboard planes, put in automobiles, and generally moved from place to place, being compact when carried and being convenient to carry.

A further object is to provide an orthopedic seat insert that enables adjustment for each individual and at any time, for quickly providing support where needed.

Another important object is to provide back support in which there is a transfer of forces from one side to the other, thereby aiding in obtaining proper back support.

Still other objects and advantages of the invention will appear from the following description.

SUMMARY OF THE INVENTION

The present invention provides a portable folding orthopedic seat unit, for use on a chair, sofa, automobile seat, airplane seat, and the like. A semirigid seat member is hinged to a back member, preferably also semirigid and comparable in over-all area to the seat member. The back and seat members can be collapsed together to a generally flat position and can be opened to a seating position. Vertical rigid support means extends from the bottom to the top of the back member, and a back-support assembly is supported adjustably, preferably slidably, on that support means. The back-support assembly comprises two separate, spaced-apart, padded, generally elliptically-shaped, back-support members, and a substantially vertically rigid and laterally flexing connecting member joining them together. Preferably, each back-support member comprises a rigid rear portion attached to the connecting member, a forward, padded, yieldable portion supported by the rear portion, and cover means enclosing both the padded portion and the rear portion. The connecting member serves to transfer forces from one back-support member to the other, as will be explained. Preferably, easily releasable locking means cooperates with the rigid support means for holding the assembly at a selected vertical position.

In a presently preferred form of the invention, a semirigid back member and a similar seat member each have a rigid quadrilateral marginal frame supporting a resilient cushion affording free air passage therethrough, and an air-permeable seat cover encloses the frame and the cushion means. Preferably, the resilient cushion comprises a first series of spaced-apart elastic bands bridging between front and back (or top and bottom) frame members and a second series of spaced-apart elastic bands bridging between a pair of side frame members, the frame members constituting the quadrilateral marginal frame.

In this presently preferred form of the invention the vertical support means may be a vertical rigid bar extending from the bottom of the marginal frame of the back member to the top thereof, on the forward surface thereof. The bar may have a series of locking recesses along each of its side edges. A carrying handle may be swivel-attached to the rigid bar near the hinge, so that it extends into the sector between the seat and the back when the unit is opened.

Also, in this presently preferred form of the invention there is one padded, generally elliptically-shaped back-support member on each side of the bar, and each back-support member comprises a rigid rear portion lying in a plane tilted outwardly from the bar at an angle of about 15° from the back member, a resilient cushion supported on the rigid portion, and a cover enclosing the cushion and the rear portion. In this particular form of the invention, readily releasable latch means is secured to the connecting member and has locking fingers that engage the locking recesses of the vertical bar, to hold the padded members at any desired height.

BRIEF DESCRIPTION OF THE DRAWINGS

In the drawings:

FIG. 3 is a view in section taken along the line 3—3 in FIG. 2. This view shows the two back-supporting members as different in structure, in order to illustrate two different types of suitable structure, although usually the two members will be identical and of either type here shown.

FIG. 4 is a view in side elevation on a reduced scale showing the chair insert folded for carrying, with the hand of a user being inserted in the handle.

FIG. 5 is a view of the chair insert of FIGS. 1-4 with its cover removed, as well as the rigid support member and the back-support assembly.

FIG. 6 is a view in perspective of a modified form of chair insert also embodying the principles of the invention.

FIG. 7 is a view in rear elevation of the chair insert of FIG. 6.

DESCRIPTION OF SOME PREFERRED EMBODIMENTS

The unit of FIGS. 1-4:

A unit 10 shown in FIGS. 1-5 illustrates a preferred embodiment of the invention, although many changes in specific construction can be made, as will be readily apparent. The unit 10 comprises a seat member 11 and a back member 12 connected together by suitable hinging means. This hinging means may comprise a pair of hinges 13 and 14 or a single piano hinge, or any suitable type of structure.

The seat member 11 may be constructed in any way desired, preferably being semirigid and having some cushioning. Different models may be made one way and other models another way so as to afford variety of choice to the purchaser.

Figure 1:
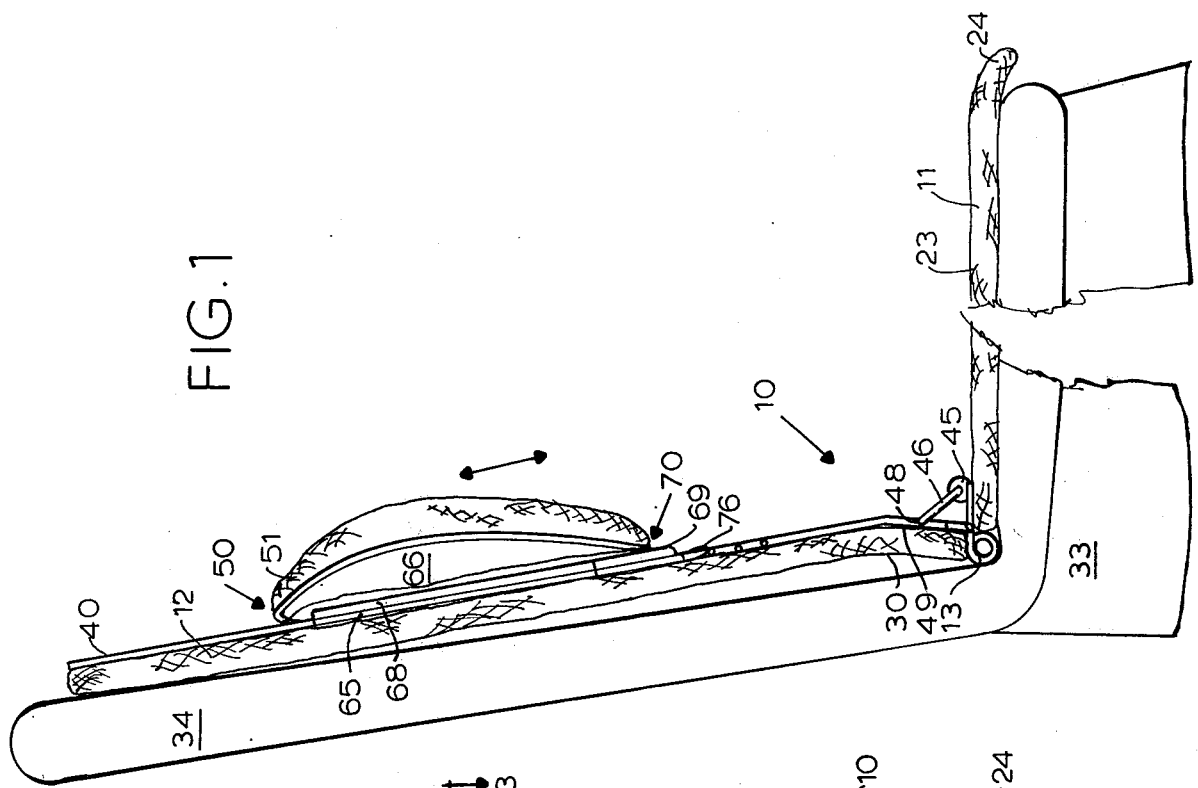
FIG. 1 is a view in side elevation of an automobile seat on which rests a portable folding orthopedic chair insert embodying the principles of the invention. The seat portion has been broken in the middle in order to conserve space, and the bottom of the automobile seat has been broken off for the same reasons.

For example, as best shown in FIG. 5, the back member 11 may have a quadrilateral rigid frame 15 with a front marginal frame member 16, a rear frame member 17, secured to the hinges 13 and 14, and side frame members 18 and 19. In between the front and rear frame members 16 and 17 extend two series of spaced-apart resilient strips or bands 20 and 21, one above the other, and in between the frame members 18 and 19 and in between the bands 20 and 21 extends a series of spaced-apart resilient strips or bands 22, preferably in two layers. The bands 20, 21, and 22 may, if desired, be interwoven. This imparts both resiliency and cushioning, and affords plenteous ventilation passages for air circulation. The frame 15 and the strips 20, 21, and 22 are then enclosed in a loosely woven cover 23 (FIGS. 1 and 2), which therefore permits relatively free flow of air for ventilation. As shown in FIG. 1 the forward portion 24 of the side frame members 18 and 19 may be bent downwardly, to increase comfort at the seat edge.

Figure 2:
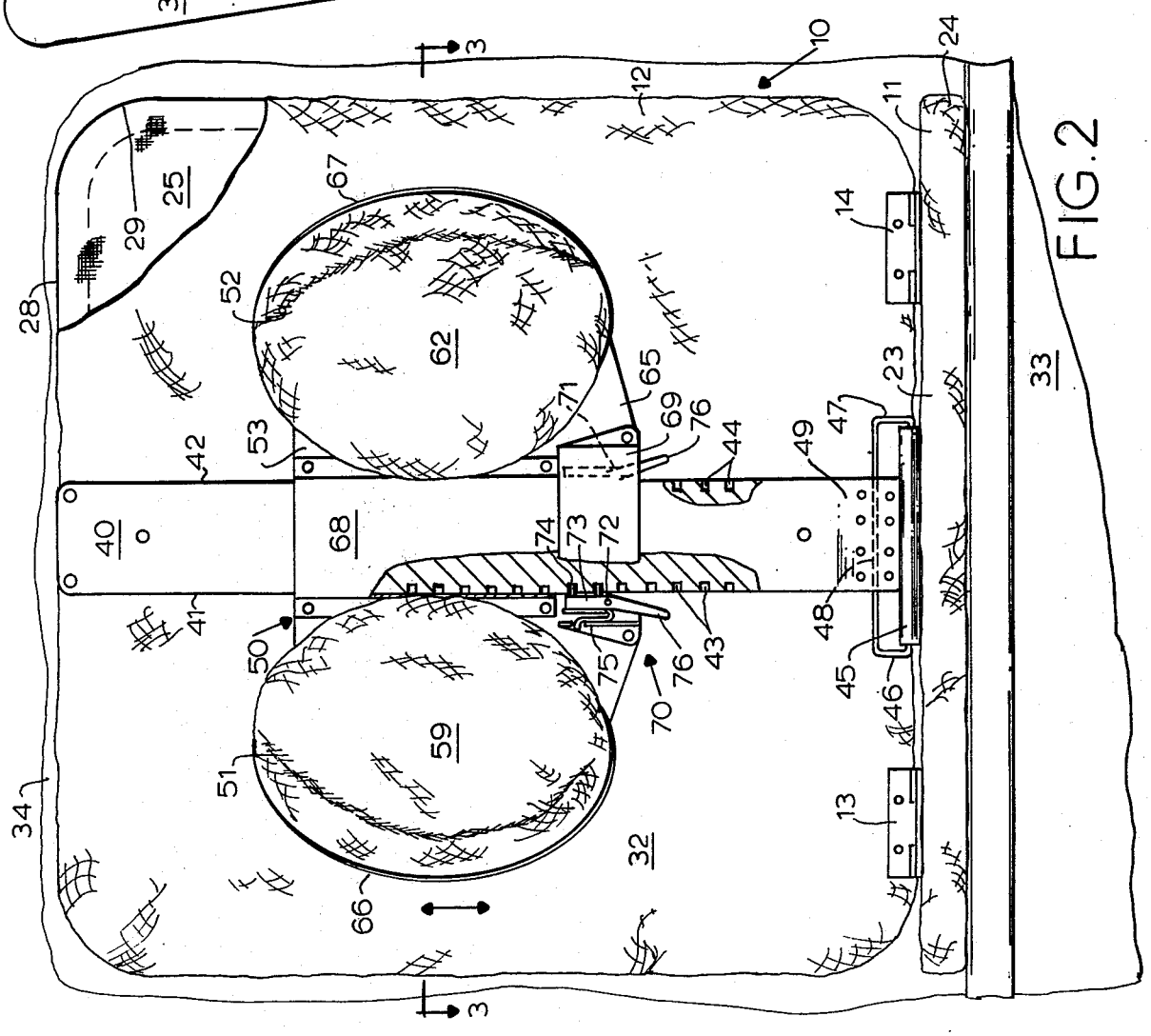
FIG. 2 is a fragmentary view in front elevation of the installation of FIG. 1, with the automobile seat cutaway to conserve space, and with portions of the chair insert cutaway to expose one side of the locking means and one corner of the back frame.

The back member 12 may be similar. As shown in FIG. 5 it may have a frame 25 with a bottom member 26 connected to the hinges 13 and 14, a top member 27, and side frame members 28 and 29. The lower portion of the side frame members 28 and 29 may comprise a bend 30 (See FIG. 1) to increase comfort. In the back 12, well-spaced resilient bands 31 extend from side to side. No vertical bands are required, though they may be used. There is thus plenty of ventilation, and the whole is enclosed in a loosely-woven cover 32 (FIGS. 1 and 2). The wide back helps to prevent the apparatus from sinking into the soft cushioning of the automobile seat back, thereby helping to transfer the proper support to the back of the user.

The novelty of the invention and its primary effect resolves both in the combination of the back 12 and the seat 11 in such a way that they support each other and help to obtain a proper positioning and also in a particular superstructure mounted on the back 12, soon to be discussed. The seat unit 10 is constructed so that the seat member 11 may rest on a regular automobile seat 33 (or a chair, sofa, or airplane seat), and the back member 12 rests against a back 34 of the seat 33. However, the seat member 11 and back member 12 may be shaped to fit into bucket seats if desired.

A rigid vertical flat bar 40 runs from the bottom frame member 26 to the top frame member 27. This bar 40 serves as a rigid support member and is also provided along each side edge 41,42 with two series of openings 43 and 44, which may be drilled thereinto. Alternately, it may have a series of teeth with notches spaced apart closely enough so that suitable adjustment can be obtained. A carrying handle 45 may enclose one end of a support ring 46 having a rod 47 extending through an opening 48 through a lower, inturned portion 49 of the bar 40. Since people are not shaped in such a way that they will engage the actual vertex between the erected back member 12 and the seat member 11, this location of the hinge causes no problems of discomfort, and it affords a good location for the handle 45 when the unit 10 is carried.

A back-support assembly 50 comprises two spaced-apart back-support members 51 and 52, preferably generally vertically oriented and preferably elliptical in shape, connected by a central, vertically rigid and laterally flexing connecting member 53.

Each of the back-support members 51 and 52 may be identical to the other, but two different forms are shown in FIG. 3. As illustrated, the member 51 has a wooden or chipboard block 54, which is rigid. The block's forward surface 55 has a slanting face portion 56, so that the block 54 is thinnest at its inner edge 57. Foam packing 58 provides a cushion, and a cover 59, preferably like the covers 23 and 32, encloses the padding 58 and the forward and side portions of the block 54. As illustrated, the other back-support member 52 has a flat, thin, rigid metal plate 60, with padding 61 and a cover 62.

The connecting member 53 is preferably thin, strong metal so that while rigid vertically it is somewhat flexible laterally, having a spring-like action tending to restore it to a central position and comprises a central portion 65 and two side portions 66 and 67 to which the block 54 and the plate 60 are respectively secured. The side portions 66 and 67 diverge from the central portion 65 at an angle, the angle preferably being about 15° (See especially FIG. 3). The edges of the covers 59 and 62 are preferably held, respectively, between the block 54 and portion 66, and between the plate 60 and the portion 67. In addition, the member 53 preferably comprises a forward central portion 68 welded to the portion 65, so that the portion 65 and 68 encompass all four sides of the bar 40. A lower portion 69 of the central portion 68 is wider than the rest and encloses most of a pair of latching devices 70 and 71. Each latching device 70 and 71 comprises a pivot pin 72 extending between the portions 65 and 68, a latch arm 73 mounted pivotally on the pin and having a locking tooth 74 for engagement in an opening 43 or 44. A spring 75 urges the latch arm 73 to normally closed position with its tooth 74 in an opening 43 and 44, while a lever portion 76 extends, preferably at an angle to the arm 73, beyond the lower edge 77 of the portion 69 so that it is accessible to the user, which grasps both lever portions 76 at once, disengaging both latch arms 73 at once by squeezing the lever portions 76 toward each other. Then he can slide the assembly 50 up or down to the proper height and by releasing the lever portion 76, enable the teeth 74 to engage openings 43 and 44 and hold the assembly 50 in place.

Each user will probably wish to adjust the proper height of the pads 51 and 52 for his body. Moreover, some people find that it is often good to shift the pad height after one has sat for a long while. One's own feelings make it clear enough which way the shift should occur. This adjustment can be made while the sitter is occupying the insert 10, by moving momentarily away from the pads 51 and 52 and then manipulating the levers 76 behind him.

When properly in place, the members 51 and 52 provide distributed support on each side of the sacrolumbar region of the spine of the user. The members 51 and 52, being separate, relieve the spine of all contact with the back and support the body on each side of the spine, distributing the supportive forces over the specific areas needing them. The cushioning portions 58 and 61 automatically accommodate to the shape of the user's back and provide proper and gentle distributed support to the lower back area. In combination with the semirigid seat bottom 11 they help him to maintain optimum posture and thereby minimize the strain on him.

Rearward pressure on and movement inward of one member 51 is transmitted through the connecting member 53 to generate a compensating forward pressure and outward movement of the other member 52, and vice versa. Thus, the assembly 50 adjusts itself to lateral and twisting movements of the user and, as a result, his precise position in the insert 10 is not critical to proper functioning of the insert 10.

A modified form of unit 80 (FIGS. 6 and 7)

A simplified and possibly less effective unit 80 is shown in FIGS. 6 and 7; it is still quite good for its main purposes.

To a seat portion 81 (which may be like the seat 11) two vertical columns 82 and 83 are connected by hinges 84 and 85, enabling folding of the unit 80. The columns 82 and 83 have a series of openings 86 to which an assembly 90 may be bolted by bolts 87 at a desired height. A cross bar 88 at the upper end joins the columns 82 and 83, while a member 89 can serve as both a handle and, if desired, as a headrest.

The back-support assembly 90 comprises two elliptical members 91 and 92 joined by a connecting member 93, or isthmus.

Operation is substantially as described before.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

We claim:

1. A portable folding orthopedic seat unit for use on a chair, automobile seat, and the like, including in combination:
    a seat member,
    a back member,
    a hinge connecting said back and seat members together so that they can be collapsed together to a generally flat position and opened to a seating position,
    said back member including vertical rigid support means extending from the bottom to the top of the back member,
    a carrying handle attached to said rigid support menns near said hinge, and
    a movable back-support assembly supported slidably on said support means and comprising:
    two separate, padded, generally elliptically-shaped, back-support members, spaced apart from each other, a substantially vertically rigid and horizontal flexing connecting member joining them together, each said back-support member comprising a rigid rear portion attached to said connecting member and extending in a plane tilted outwardly at an angle to the plane of said back member, a forward resilient portion supported on said rear portion, and cover means enclosing said resilient portion and said rear portion, and
    means for holding said connecting member at a desired adjustable vertical position on said rigid support means,
    whereby the back of the person sitting in said portable seat unit is supported solely by said two separate back-support members.

2. The seat unit of claim 1 wherein said vertical rigid support means comprises a flat centrally positioned bar, said connecting member being slidably mounted thereon, said releasable locking means being mounted on said connecting member.

3. A portable folding orthopedic seat unit for use on a chair, automobile seat, and the like, including in combination:
    a semirigid seat member,
    a back member comparable in over-all area to the seat member,
    a hinge connecting said back and seat members together so that they can be collapsed together to a generally flat position and opened to a seating position,
    a carrying handle attached near the hinge and extending into the sector between the seat and the back when the unit is opened,
    a vertical rigid bar extending centrally from the bottom to the top of the back member, and
    a movable back-support assembly, comprising two separate, padded, generally elliptically-shaped, back-support members, one on each side of said bar, and a substantially vertically rigid and laterally flexing member joining them together, and slidably mounted on said bar for support thereby and vertical movement therealong,
    each said back-support member comprising a rigid rear portion lying in a plane tilted at an angle away from said back member with its edge adjacent said bar being closer to the back member than is its opposite edge, padding supported on the rigid member, and cover means enclosing said padding and said rear portion, and locking means for releasably locking said rigid member in any desired vertical position to said vertical bar.

4. A portable folding orthopedic seat unit, including in combination:

a seat member having a rigid quadrilateral marginal frame, resilient air-permeable cushion means supported by said frame, and an air-permeable seat cover enclosing said frame and said cushion means, a back member comparable in over-all area to the seat member, having a rigid quadrilateral marginal frame, resilient air-permeable cushion means, supported by said frame and an air-permeable cover enclosing said frame and said cushion means, said back member having a forward surface, a hinge connecting said back and seat members together so that they can be collapsed together to a generally flat position and opened to a seating position, a vertical rigid bar extending from the center of the bottom of said marginal frame of the back member, to the center of the top thereof closely adjacent the forward surface thereof, said bar having a series of locking recesses, a carrying handle swivel-attached to said rigid bar near the hinge and lying in the sector between the seat and the back when the unit is opened, and a movable back-support assembly comprising two spaced-apart padded, generally elliptically-shaped back-support members, one on each side of said bar, and a substantially vertically rigid and laterally flexing connecting member joining them together and slidably mounted on said bar for support thereby of said assembly and for vertical movement therealong, each said back-support member comprising a rigid rear portion lying in a plane tilted outwardly from said bar at an angle of about 15° from the back member, padding supported on said rigid rear portion, and cover means enclosing said padding and said rear portion, each said back-support member extending out forwardly a substantial distance beyond said bar so that they alone come into contact with the back of a person seated on said portable unit, said connecting member having secured thereto releasable latch means for releasably engaging the locking recesses of said vertical bar to hold said movable assembly at any desired height along said bar.

5. The seat unit of claim 4, wherein said resilient cushion means comprises at least one series of spaced-apart elastic bands bridging between two generally parallel frame members of said quadrilateral marginal frame.

* * * * *